(12) United States Patent
Reid

(10) Patent No.: US 7,584,755 B2
(45) Date of Patent: \*Sep. 8, 2009

(54) MULTIPLE SLEEVE METHOD AND APPARATUS FOR TREATING EDEMA AND OTHER SWELLING DISORDERS

(76) Inventor: Tony Reid, P.O. Box 7433, Menlo Park, CA (US) 94025

( \* ) Notice: Subject to any disclaimer, the term of this patent is extended or adjusted under 35 U.S.C. 154(b) by 269 days.

This patent is subject to a terminal disclaimer.

(21) Appl. No.: 10/725,837

(22) Filed: Dec. 1, 2003

(65) Prior Publication Data

US 2004/0111047 A1 Jun. 10, 2004

Related U.S. Application Data

(63) Continuation of application No. 09/152,782, filed on Sep. 14, 1998, now Pat. No. 6,656,141, which is a continuation-in-part of application No. 08/860,430, filed on Sep. 5, 1997, now Pat. No. 5,916,183, which is a continuation-in-part of application No. 08/390,866, filed on Feb. 17, 1995, now abandoned.

(51) Int. Cl.
*A61F 13/10* (2006.01)
*A61F 13/06* (2006.01)

(52) U.S. Cl. ............... 128/878; 128/882; 128/845; 128/846; 128/869; 602/5; 602/13; 602/20; 602/62; 602/63

(58) Field of Classification Search ............. 601/134, 601/151, 152; 602/5, 13, 20, 23, 60–65; 128/845, 896, DIG. 20, 846, 878, 882
See application file for complete search history.

(56) References Cited

U.S. PATENT DOCUMENTS

| 800,467 A | 9/1905 | Myers |
| 814,795 A | 3/1906 | Myers |
| 1,226,013 A | \* 5/1917 | Roth .................. 602/40 |
| 2,533,504 A | 12/1950 | Poor |
| 2,699,165 A | 1/1955 | Ferrier |
| 2,781,041 A | 2/1957 | Weinberg |
| 2,823,668 A | 2/1958 | Van Court |
| 2,943,859 A | 7/1960 | Koski et al. |
| 3,173,420 A | 3/1965 | Mazzoni et al. |
| 3,186,405 A | 6/1965 | Bailey et al. |
| 3,454,010 A | 7/1969 | Lilligren et al. |
| 3,464,010 A | 8/1969 | Saul |
| 3,561,435 A | 2/1971 | Nicholson |
| 3,728,875 A | 4/1973 | Hartigan et al. |
| 3,845,769 A | 11/1974 | Shaw |
| 3,850,167 A | 11/1974 | Seeley |

(Continued)

FOREIGN PATENT DOCUMENTS

GB 1531268 12/1975

*Primary Examiner*—Justine R Yu
*Assistant Examiner*—Clinton Ostrup
(74) *Attorney, Agent, or Firm*—Townsend and Townsend and Crew LLP

(57) ABSTRACT

An apparatus for applying pressure to a body part comprising: a first sleeve comprising a multiplicity of pressure-applying resilient protrusions configured to apply a therapeutic pressure to a surface of the body part of a patient; and a second sleeve slidably received over the first sleeve, the second sleeve configured to apply a pressure to the first sleeve, thereby increasing the therapeutic pressure applied by the first sleeve on the limb.

10 Claims, 10 Drawing Sheets

U.S. PATENT DOCUMENTS

| | | | |
|---|---|---|---|
| 3,856,008 A | 12/1974 | Fowler et al. | |
| 3,862,629 A | 1/1975 | Rotta | |
| 3,885,554 A | 5/1975 | Rockwell, Jr. | |
| 3,888,242 A | 6/1975 | Harris et al. | |
| 3,892,239 A | 7/1975 | Masso Remiro | |
| 3,942,518 A | 3/1976 | Tenteris et al. | |
| 3,975,929 A | 8/1976 | Fregeolle | |
| 3,990,437 A * | 11/1976 | Boyden et al. | 602/8 |
| 4,013,069 A | 3/1977 | Hasty | |
| 4,030,488 A | 6/1977 | Hasty | |
| 4,150,442 A | 4/1979 | Boone | |
| 4,157,713 A | 6/1979 | Clarey | |
| 4,180,065 A | 12/1979 | Bowen | |
| 4,186,738 A | 2/1980 | Schleicher | |
| 4,215,687 A | 8/1980 | Shaw | |
| 4,315,504 A | 2/1982 | Drennan | |
| 4,320,746 A | 3/1982 | Arkans et al. | |
| 4,338,923 A | 7/1982 | Gelfer et al. | |
| 4,369,588 A | 1/1983 | Berguer | |
| 4,370,975 A | 2/1983 | Wright | |
| 4,374,518 A | 2/1983 | Villanueva | |
| 4,383,342 A | 5/1983 | Forster | |
| 4,402,312 A | 9/1983 | Villari et al. | |
| 4,421,110 A | 12/1983 | DeLisle et al. | |
| 4,469,095 A * | 9/1984 | Herrera | 602/63 |
| 4,552,133 A | 11/1985 | Kawaguchi | |
| 4,573,456 A | 3/1986 | Spann | |
| 4,583,522 A | 4/1986 | Aronne | |
| 4,738,249 A | 4/1988 | Linman et al. | |
| 4,773,397 A | 9/1988 | Wright et al. | |
| 4,922,893 A | 5/1990 | Wright et al. | |
| 4,938,208 A | 7/1990 | Dye | |
| 4,945,903 A | 8/1990 | Alper | |
| 4,961,418 A | 10/1990 | McLaurin-Smith | |
| 4,971,041 A | 11/1990 | Millikan et al. | |
| 5,014,681 A | 5/1991 | Neeman et al. | |
| 5,063,910 A | 11/1991 | Cartier | |
| 5,108,426 A | 4/1992 | Biro et al. | |
| 5,109,832 A | 5/1992 | Proctor | |
| 5,117,812 A | 6/1992 | McWhorter | |
| 5,171,211 A * | 12/1992 | Deasy, Jr. | 602/61 |
| 5,172,689 A | 12/1992 | Wright | |
| 5,228,142 A | 7/1993 | Yoswein-McGreen | |
| 5,233,974 A | 8/1993 | Senoue et al. | |
| 5,257,956 A | 11/1993 | Ewen | |
| 5,310,400 A | 5/1994 | Rogers et al. | |
| 5,403,265 A | 4/1995 | Berguer et al. | |
| 5,474,525 A * | 12/1995 | Blott | 602/63 |
| 5,497,513 A | 3/1996 | Arabeyre et al. | |
| 5,591,200 A | 1/1997 | Cone et al. | |
| 5,592,953 A * | 1/1997 | Delao | 128/882 |
| 5,916,183 A | 6/1999 | Reid | |
| 5,976,099 A | 11/1999 | Kellogg | |

* cited by examiner

MULTIPLE SLEEVE METHOD AND APPARATUS FOR TREATING EDEMA AND OTHER SWELLING DISORDERS

CROSS-REFERENCES TO RELATED APPLICATIONS

This application is a continuation of application Ser. No. 09/152,782, filed Sep. 14, 1998 (now U.S. Pat. No. 6,656, 141), which was a continuation-in-part of application Ser. No. 08/860,430, filed on Jun. 24, 1997 (now U.S. Pat. No. 5,916, 183), which is a continuation-in-part of application Ser. No. 08/390,866, filed on Feb. 17, 1995 (now abandoned), all in the name of the present assignee, and all hereby incorporated by reference for all purposes.

BACKGROUND OF THE INVENTION

1. Field of the Invention

The present invention relates generally to medical devices and methods, and in particular to a device and method for removing edema fluids from a body trunk and/or extremity such as an arm or a leg.

Breast cancer is a serious disease in women, and a variety of modalities are employed in its treatment. Many of these treatments result in damage to the lymphatic and/or venous system which, in turn, can cause a condition referred to as "lymphedema." Lymphedema is the accumulation of excessive lymph fluid and swelling of subcutaneous tissues due to the obstruction or destruction of lymph vessels. In breast cancer patients, lymphedema occurs in the arm and results in painful swelling. Excessive fluid accumulation, referred to as edema, can also arise in the arms, legs and, trunk from a variety of other causes, including infection, radiation therapy, and other conditions which result in damage to or destruction of portions of the lymphatic and/or venous system.

2. Description of the Background Art

A variety of devices and methods have been proposed for the treatment of lymphedema in the arms and elsewhere. Many such devices utilize a sequential pump which works like a multiplicity of blood pressure cuffs extending from the shoulder to the hand, which contract and expand individually. When pressure is exerted by any one chamber or cuff, it applies a 'blanket pressure' (i.e. an annular pressure which completely circumscribes the limb or other body portion) to the skin directly underneath the area of that chamber. When the pressure upon that area is released, a similar blanket pressure is then applied to the portion of the arm covered by the next adjacent chamber, and so on up the arm. Such blanket pressures are applied sequentially from the distal to the proximal ends of the arm, with the intention of forcing the fluids up the arm and into the trunk of the body, where existing lymph nodes can process them.

Another prior mode of treatment has been a double walled sheath or stocking in which air pressure is introduced between the walls to squeeze the limb. It has been found that this and other similar systems, which rely on uniform blanket pressure application through the length of the afflicted limb or portions thereof, do not perform very well and in fact may interfere with the desired distal-to-proximal flow of lymphatic fluid.

We have found that when a uniform and/or excessive pressure is applied to an area for the purpose of moving fluid, the opposite effect may result. In particular, the application of pressure may: 1) compress the veins and lymph ducts, resulting in blockage; 2) augment capillary leak; and 3) prevent the lymphatic fluids from mobilizing.

Other approaches to treatment have included employment of a sheath that is separated into a number of longitudinally spaced inflatable air cells encircling the limb to be treated. These cells are successively inflated with uniform air pressure from the distal end to the proximal end of the sheath with the intent of promoting fluid flow in the desired direction. Such systems have been largely ineffectual, as they rely on air pressure being maintained at the same level or magnitude in any one of, or all, of the pressurized cells, producing a blanket effect. U.S. Pat. Nos. 2,533,504 and 2,781,041 disclose examples of such systems.

Prior U.S. Pat. No. 4,370,975 discloses an apparatus for treating lymphedema and similar fluid retention afflictions through the use of a multi-cell inflatable sheath which encompasses the swollen limb. Pressure is applied in the cells of the sheath in timed sequence from the distal cell to the proximal cell, the sequence of pressure applied also defining a decreasing gradient pressure from a maximum pressure applied in the distal cell to a minimum pressure applied in the proximal cell when all of the cells are pressurized. Generally, for each of the adjacent cells the more distal has applied a higher pressure than the more proximal. This application of gradient pressure from distal to proximal cells in time sequence comprises a cycle, and such cycle may be repeated indefinitely to promote the flow of lymphatic fluid from the afflicted limb in a proximal direction.

The problem with the above methods is that any form of blanket pressure such as that applied by pneumatic or hydraulic pressure to large afflicted areas will have at best a minimal result.

Carter, U.S. Pat. No. 5,063,910 shows an apparatus for treating vascular, metabolic and functional imbalance of a limb by variations in pressure of a high-density fluid, such as a mercury bath, around the limb.

The problem with this device is that the pressure applied by this means is, in fact, a blanket-pressure, which increases with the depth of the limb portion within the fluid bath, resulting in the disadvantages described above for al other pressure systems. Another disadvantage is that the patient must remain immobilized during treatment.

R. W. Lilligren et al, U.S. Pat. No. 3,454,010, shows a hollow tube-like bandage for wrapping in a spiral-like manner around the limb of a patient, into which is then applied a pneumatic pressure, which is intended to drive out excess fluids prior to surgery.

Once again the pressure applied is a uniform or blanket pressure to the skin, and so is relatively ineffective to reduce swelling.

Ewen, U.S. Pat. No. 5,257,956, shows a garment for use by post-mastectomy patients which alleviates post-operative pain and discomfort and facilitates normal activity during the recovery period. A padded vest-like garment is adapted for applying comforting pressure to the sites of removal of breast and other tissues and for holding pain relieving packages.

Again, the problem with this garment is that it applies a blanket pressure, resulting in little reduction in swelling.

Fregealle, U.S. Pat. No. 3,975,929, shows a stocking knit on a circular knitting machine which provides a gradually decreasing compressive force on the leg of the of the wearer from the ankle upwardly to the top of the stocking. Again, we believe that a uniform or blanket-pressure such as is applied by this device, is not the best method for forcing out excess lymphedema fluids.

In all of these pressure-applied methods, the patient is immobilized up to 4 hours per day, and sometimes several days in succession, suffering following treatment and soreness of the arm for many days afterwards.

It is a well established fact that special exercises following mastectomy help to mobilize lymphedema fluids; yet prior art devices contribute toward immobilizing the patient, making exercising difficult or impossible. Thus resulting in a counter-producing effect.

The cost of sequential pumps including necessary limb compression apparatus range from $500 to over $8,000. In addition, skilled technicians are necessary to operate it, thereby making treatment for lymphedema patients extremely expensive.

The following cited prior art references are relevant but distinguished from the present invention: U.S. Pat. Nos. 2,533,504, 2,699,165, 2,781,041, 2,943,859, 3,173,420, 3,454,010, 6,548,819, 3,561,435, 3,728,875, 3,845,769, 3,862,629, 3,885,554, 3,942,518, 3,975,929, 4,013,069, 4,030,488, 4,180,065, 4,320,746, 4,370,975, 4,374,518, 4,402,312, 4,552,133, 4,583,522, 4,773,397, 4,922,893, 4,938,208, 4,961,418, 5,108,426, 5,109,832, 5,117,812, 5,171,211, 5,172,689, 5,228,142, 5,233,974, 5,257,956 and 5,310,400.

BRIEF SUMMARY OF THE INVENTION

The present invention provides improved apparatus and methods for treating body parts of the patient, particularly the limbs, to relieve swelling due to lymphedema and other causes. The apparatus comprises a plurality of sleeves received one over another onto a patient's limb. The innermost sleeve comprises a therapeutic pressure sleeve. In various embodiments of the present invention, a secondary sleeve, (which is slipped over the therapeutic pressure sleeve), comprises a thin fabric compression sleeve. In alternate embodiments, the secondary sleeve comprises an inflatable compression sleeve. In still further alternate embodiments, both a thin fabric compression sleeve and an inflatable compression sleeve are received over the therapeutic pressure sleeve.

When using either the thin fabric compression or inflatable compression sleeve as the secondary sleeve, the inner therapeutic pressure sleeve is first pulled into position over the patient's limb. Thereafter, the secondary sleeve is pulled into position over the therapeutic pressure sleeve. As will be explained, the therapeutic pressure sleeve exerts a therapeutic pressure at select locations on the patient's limb. The secondary sleeve exerts a pressure on the inner therapeutic pressure thereby increasing the therapeutic pressure on the patient's body surface. In certain preferred embodiments, both a thin fabric compression sleeve and an inflatable compression sleeve are simultaneously used, with the inflatable compression sleeve received over the thin fabric compression sleeve. In such embodiments, the inflatable compression sleeve exerts a pressure on the thin fabric compression sleeve which in turn exerts a pressure on the therapeutic pressure sleeve, thereby increasing the therapeutic pressure applied to the patient's limb.

In one preferred embodiment, the secondary sleeve is formed of a thin fabric sheet of elastically deformable material having a diameter somewhat smaller than the outer diameter of the therapeutic pressure sleeve. Accordingly, such a thin fabric compression sleeve is dimensioned to fit tightly around the therapeutic pressure sleeve. The thin fabric compression sleeve is circumferentially stretched when slipped into position over the therapeutic pressure sleeve. The natural elastic tendency of the thin fabric compression sleeve to constrict will exert a pressure on the therapeutic pressure sleeve, thereby increasing the therapeutic pressure exerted by the therapeutic pressure sleeve on the patient's limb. In this embodiment of the secondary sleeve, the therapeutic pressure and thin fabric compression sleeve materials are selected such that the coefficient of friction between the therapeutic pressure sleeve and thin fabric compression sleeve is sufficiently low such that the thin fabric compression sleeve can easily be slipped on (and off) over the therapeutic pressure sleeve after the therapeutic pressure sleeve has already been slipped onto the patient's limb. By using a therapeutic pressure and a thin fabric compression sleeve together, a higher therapeutic pressure can comfortably be applied to the patient's limb than could comfortably be applied by one tightly fitting elastically deformable therapeutic pressure sleeve alone. This is due to the fact that should only one elastically deformable therapeutic pressure sleeve instead be used, this sleeve would have to be dimensioned to be initially tightly received over the limb, thus being difficult for the patient to comfortably slip on and off.

Another advantage of using thin fabric compression sleeves is that more than one thin fabric compression sleeve can be used simultaneously. Should two or more thin fabric compression sleeves be used, the additional outer sleeves can be received over the inner sleeves such that the addition or removal of the outer sleeves can be used as a means of pressure adjustment. Moreover, when using such thin fabric outer compression sleeves, these sleeves can be made to shorter lengths than the inner therapeutic pressure sleeve such that one or more of these shorter sleeves can be received only over particular length portions of the patient's limb, as desired. Accordingly, bands of different therapeutic pressures can be simultaneously maintained at different locations on the patient's limb.

In another embodiment, the secondary sleeve comprises an inflation device such as an inflatable bladder. Inflation of such a sleeve causes the inflatable compression sleeve to expand such that the inner surface of the sleeve exerts a pressure on the outer surface of the inner therapeutic pressure sleeve, thereby increasing the therapeutic pressure delivered to the patient. When initially deflated, the inflatable compression sleeve may therefore be dimensioned to be initially loosely received over the therapeutic pressure sleeve. An advantage of such a secondary inflatable sleeve received over the therapeutic pressure sleeve is that it is possible to easily adjust the therapeutic pressure applied to the limb by adjusting the inflation pressure in the inflatable compression sleeve.

In addition, when using an inner therapeutic pressure sleeve within a periodically inflating and deflating outer inflatable compression sleeve, the pressure range exerted by the inflatable compression sleeve can be attenuated, while still maintaining a therapeutic pressure on the patient's limb. Specifically, the inner therapeutic sleeve will maintain a baseline therapeutic pressure on the limb even when the outer inflatable compression sleeve is intermittently deflated. Moreover, the inner therapeutic pressure sleeve will also operate to limit the maximum pressure applied to the limb when the inflatable compression sleeve is inflated. Furthermore, a gentler rate of increase and a gentler rate of decrease in the net pressure applied to the limb by the inflatable compression sleeve will be achieved by the use of an inner therapeutic pressure sleeve within an inflatable compression sleeve. Accordingly, a very beneficial therapeutic massaging effect can be generated.

In certain embodiments, the inflatable compression sleeve may have separate pressurized compartments such that different levels of therapeutic pressure may be applied to different portions of the patient's limb. The pressures in the various compartments may themselves be varied such that a therapeutic massaging effect is generated.

In all of the various embodiments of the present invention, the use of a plurality of separate sleeves has numerous advantages including ease of adjusting the pressure on the patient's limb. In particular, receiving an additional sleeve or sleeves over the therapeutic pressure sleeve will increase the pressure on the patient's limb to various pre-determined pressures dependant upon the number, dimensions, material and/or inflation pressure of the additional outer sleeve(s). Since the pressure applied to the patient's limb can be altered by adding or removing an outer sleeve or sleeves, or by varying the inflation pressure of the inflatable compression sleeve, optimal therapeutic pressures can be tailored to each individual patient's needs, which may vary over time and may also vary from one location to another on the patient's limb.

Another advantage of the present use of multiple sleeves is ease of manufacturing since additional fastening elements are not required to "close" or "tighten" the therapeutic pressure or secondary sleeves. Accordingly, the use of VELCRO straps or zippers is avoided. Rather, the dimension and construction of the sleeves themselves is itself sufficient to produce an appropriately high pressure therapeutic device.

The therapeutic pressure sleeve provides a therapeutic system of applying pressure at select locations on the patient's limbs such that lymphedema, edema and other swelling disorders are treated, as follows. The therapeutic pressure sleeve comprises a multiplicity of pressure-applying resilient protrusions such as fingers or ridges which are arranged to apply inward pressure onto a surface of the body part to relieve swelling. The protrusions will be formed from a compressible material, such as foam rubber, and pressure will be applied by wrapping or otherwise compressing or collapsing the protrusions onto the body portion so that the fingers apply a controlled level of pressure onto a localized area over the body part surface. In all embodiments, the protrusions will be spaced-apart in an array so that the tips of the fingers or ridges which engage the body part surface apply pressure in a spaced-apart manner. Surprisingly, it has been found that applying such a distributed pattern of spaced-apart pressure points or lines against the skin effectively reduces swelling resulting from lymphedema and other edemas in a simple and cost-effective manner. In particular, the method and apparatus of the present invention do not block or inhibit fluid flow within the body part, further enhancing the body's ability to resorb the fluid responsible for swelling. An additional advantage of the device is that it is both simple and comfortable to use, enhancing patient compliance. In the treatment of lymphedema, the apparatus and method of the present invention have particularly been found to permit the release and flow back of fluid to the remaining healthy lymph nodes in a controlled manner that does not overburden such collateral lymphatic drainage.

In a specific embodiment of the present invention intended for use with the limbs of the body, i.e., the arms and legs, the resilient protrusions will have a height from a radially outward base to a radially inward tip in the range from 0.5 cm to 15 cm. The protrusions are arranged in a generally cylindrical envelope with individual fingers or ridges being aligned radially inwardly with respect to the axis of the cylindrical envelope. The length of the cylindrical envelope will depend on the body part being treated, e.g. from about 3 cm for a finger to 200 cm for trunk and legs. In an apparatus intended specifically for use with an arm, the length of the cylindrical envelope is in the range from 10 cm to 90 cm, the bases of the fingers are distributed over a generally cylindrical surface having a diameter in the range from 7.5 cm to 75 cm, and the tips of the fingers are distributed over a generally cylindrical surface having a diameter in the range from 2 cm to 15 cm. The diameters, of course, will vary widely for treatment of other body parts. The innermost therapeutic pressure sleeve will preferably comprise at least an outer covering, preferably formed of material such as NYLON, having a low coefficient of friction. The outer covering secures the base of the fingers over the generally cylindrical outer surface. The outer covering may generally be formed from any suitable material which permits the fingers or ridges to be rolled to form the generally cylindrical envelope. The therapeutic pressure sleeve may further comprise an inner lining, preferably formed of SPANDEX. The inner lining covers the radially inward tips of the fingers over a generally cylindrical surface. The inner lining will be intended primarily for comfort and cleanliness and will be formed from any suitably soft, relatively thin material which allows the resilient fingers to apply pressure to the body part surface.

In a more specific embodiment, the resilient protrusions will be provided by a sheet of convoluted plastic foam which, when unrolled, has a plurality of protuberances projecting upwardly from a base surface thereof. The protuberances typically form cylindrical fingers or axially aligned ridges which are tapered to a smaller width in the direction away from their base. The sheet of plastic foam can be rolled into the desired cylindrical envelope configuration described above. The tapering of the protrusions is a particular advantage since it permits rolling of the foam rubber sheet with excessive compression of the inner surface of the sheet.

A principle feature of the present invention is the provision of an improved device for applying pressure to a patient's limb for the purpose of facilitating the flow of lymphedema fluid up the limb to the shoulder or hip. This feature includes a therapeutic pressure sleeve which can be slipped over the patient's limb and which contains a multiplicity of inwardly-pointed pressure-applying resilient fingers or ridges. The fingers are preferably arranged in rows, and the rows are arranged side-by-side such that the fingers form a grid pattern having space around each finger and between the rows. Each finger individually exerts pressure against a small area of the skin, and each small area is separated by space. The separation of individual fingers is an advantage particular in that it allows for more precise control of pressure and pressure gradient applied to the body surface.

Another feature of the present invention is that each resilient finger protrusion in the therapeutic pressure sleeve provides controlled pressure against the adjacent body surface, which in turn allows the fluid to be mobilized back to the lymphatic and venous system. It is important that the applied pressure be sufficiently great to promote flow of excess fluid from tissue back into vascular (venous and lymphatic) circulation and thereby reduce swelling. It is equally important that the applied pressure not be so large that fluid is impeded from returning to vascular circulation. It has been found that an applied pressure in the range from 5 mmHg to 60 mmHg is usually sufficient, preferably from 10 mmHg to 45 mmHg. The precise applied pressure will usually be slightly lower than venous and lymphatic outflow pressure, typically being about 1 mmHg to 10 mmHg below the individual patient's venous pressure.

In accordance with the present invention, the therapeutic pressure sleeve can be fabricated to exert a pressure in the range of 5 mmHg to 30 mmHg, and the secondary sleeve can be formed to exhibit an additional pressure in the range of 5 mmHg to 30 mmHg, thereby increasing the total therapeutic pressure on the limb to 10 mmHg to 60 mmHg. Generally, higher maximum pressures (such as 60 mm Hg) are applied to the patient's legs, and lower maximum pressures (such as 50 mm Hg) are applied to the patient's arms.

The devices of the present invention have been found to be particularly suitable for maintaining the desired controlled pressures needed for the treatment methods. In particular, use of the therapeutic pressure sleeve's inner foam layer allows the compressive force to be applied while permitting significant body movement. While other devices, such as an elastic covering, could initially be set at a desired pressure, body movement such as arm flexing, would result in tight constriction of the fluid circulation. Use of the resilient protuberances is particularly preferred since it allows rolling of the device over the body part without excessive compression of the inner surface of the material. Other foam and resilient materials, however, could also be used, e.g. foams which are less dense near the surface which engages the body part.

Another feature of the present invention is the application of the apparatus to the hand in the form of a glove, or the chest or back, in the form of a vest.

Further features will become apparent in the following description of the embodiments of this invention and from the appended claims.

DETAILED DESCRIPTION OF THE INVENTION

Figure 1:
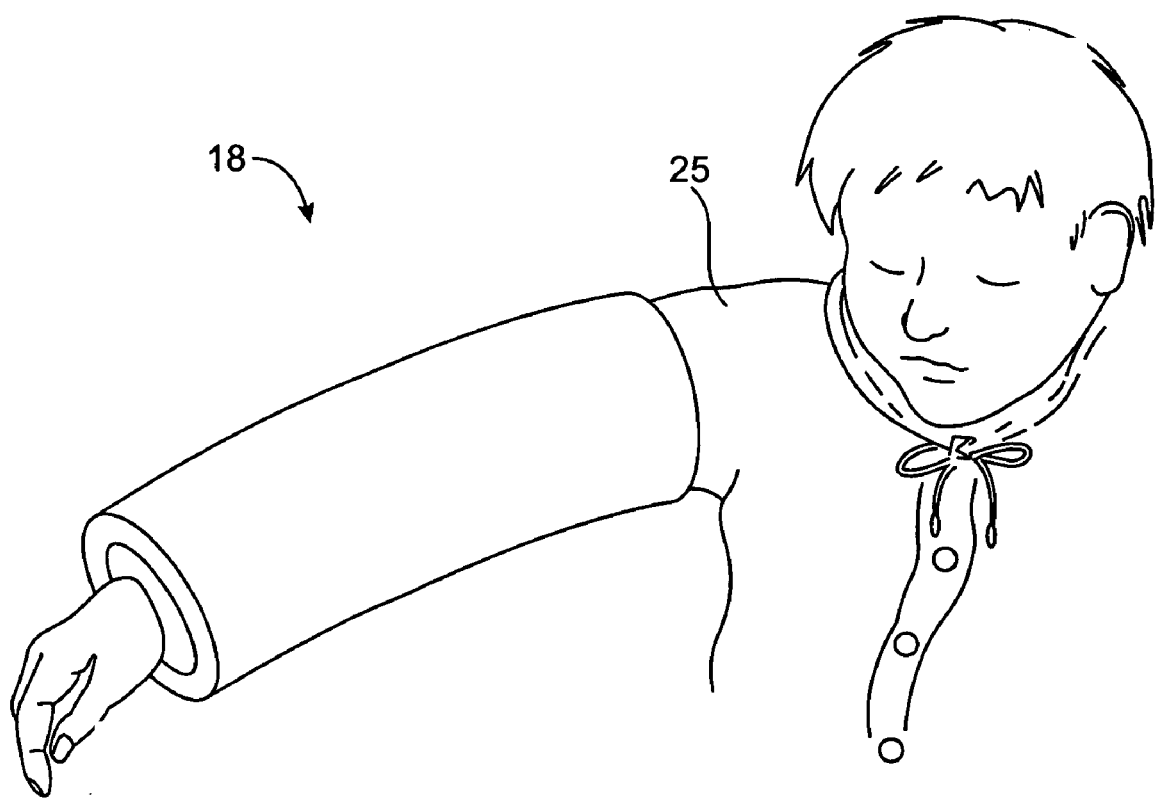
FIG. 1 is a perspective view of the therapeutic pressure sleeve of the present invention fitted onto a patient's arm.
Figure 2A:
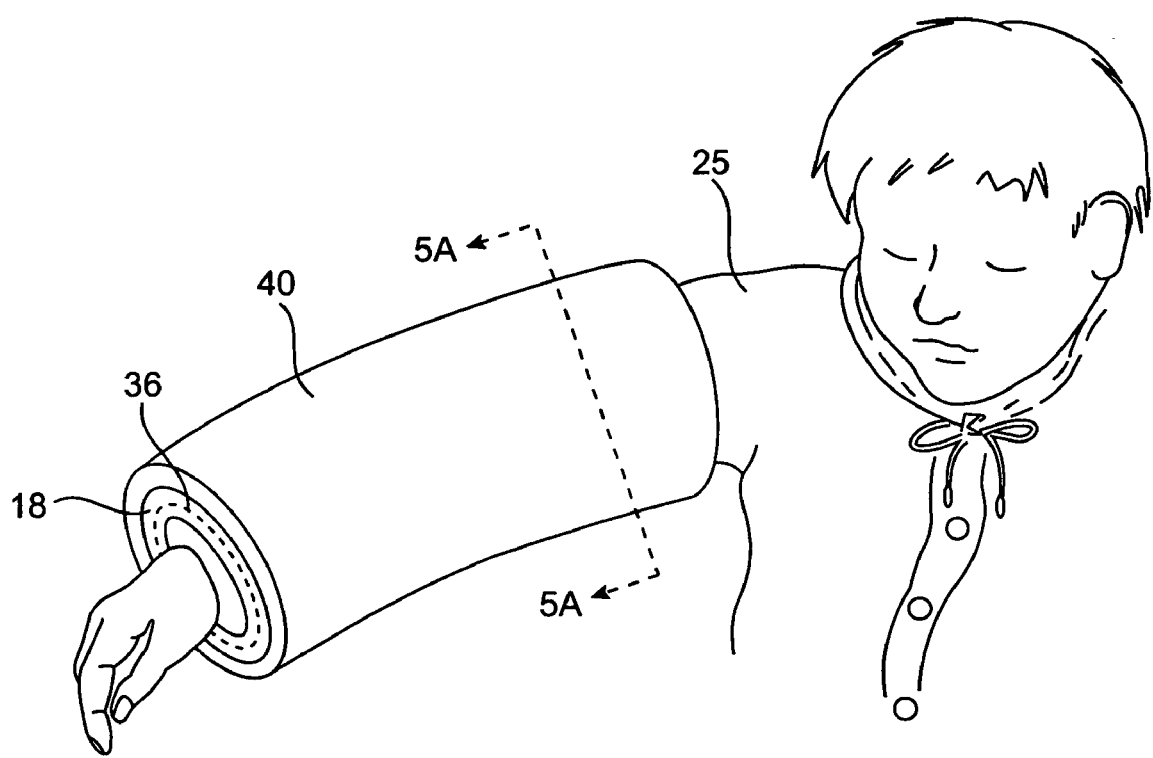
FIG. 2A is a view corresponding to FIG. 1, but with a thin fabric compression sleeve received over the therapeutic pressure sleeve.
Figure 2B:
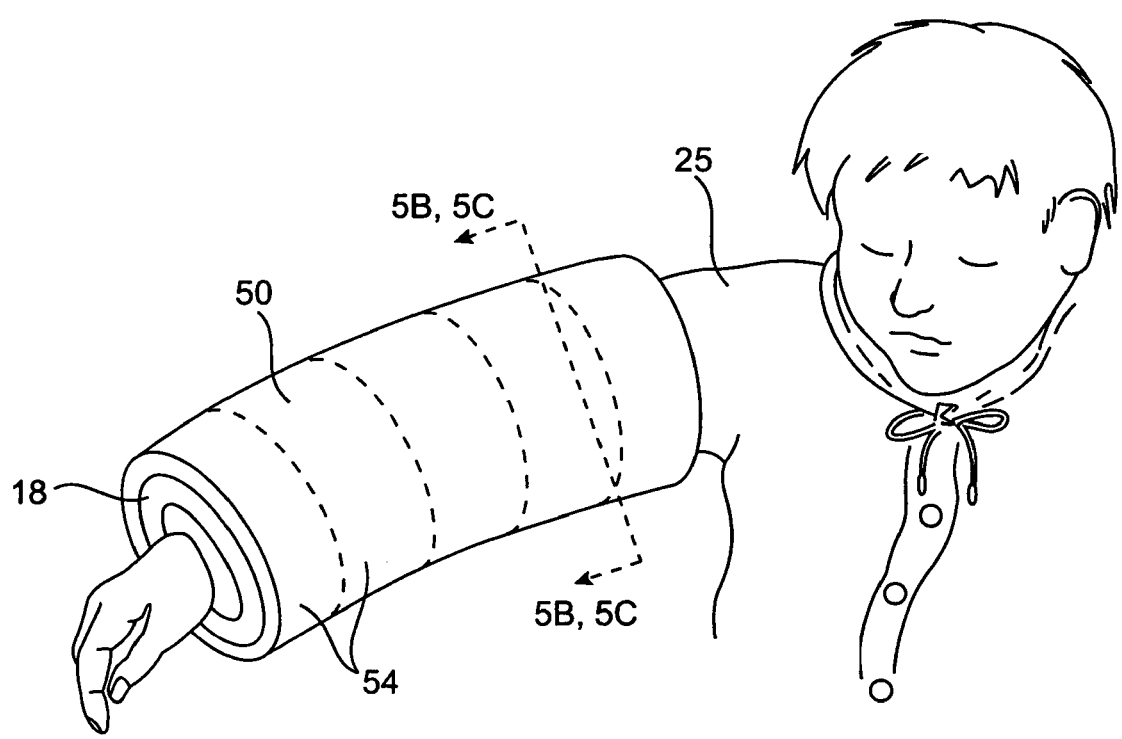
FIG. 2B is a view corresponding to FIG. 1, but with an inflatable compression sleeve received over the therapeutic pressure sleeve.

FIG. 1 shows the therapeutic pressure sleeve apparatus 18 of the present invention fitted onto a patient's arm for treating lymphedema. (It is to be understood, however, that the present invention can also be fitted to the patient's leg, hand, foot or torso). As will be explained, sleeve 18 is preferably received within a secondary sleeve which exerts a pressure on sleeve 18 such that an increased therapeutic pressure is applied to the patient's body surface. Various embodiments exist for the secondary sleeve. For example, FIG. 2A shows a thin fabric compression sleeve 40 received over sleeve 18 and FIG. 2B shows an inflatable compression sleeve 50 received over sleeve 18.

Figure 3:
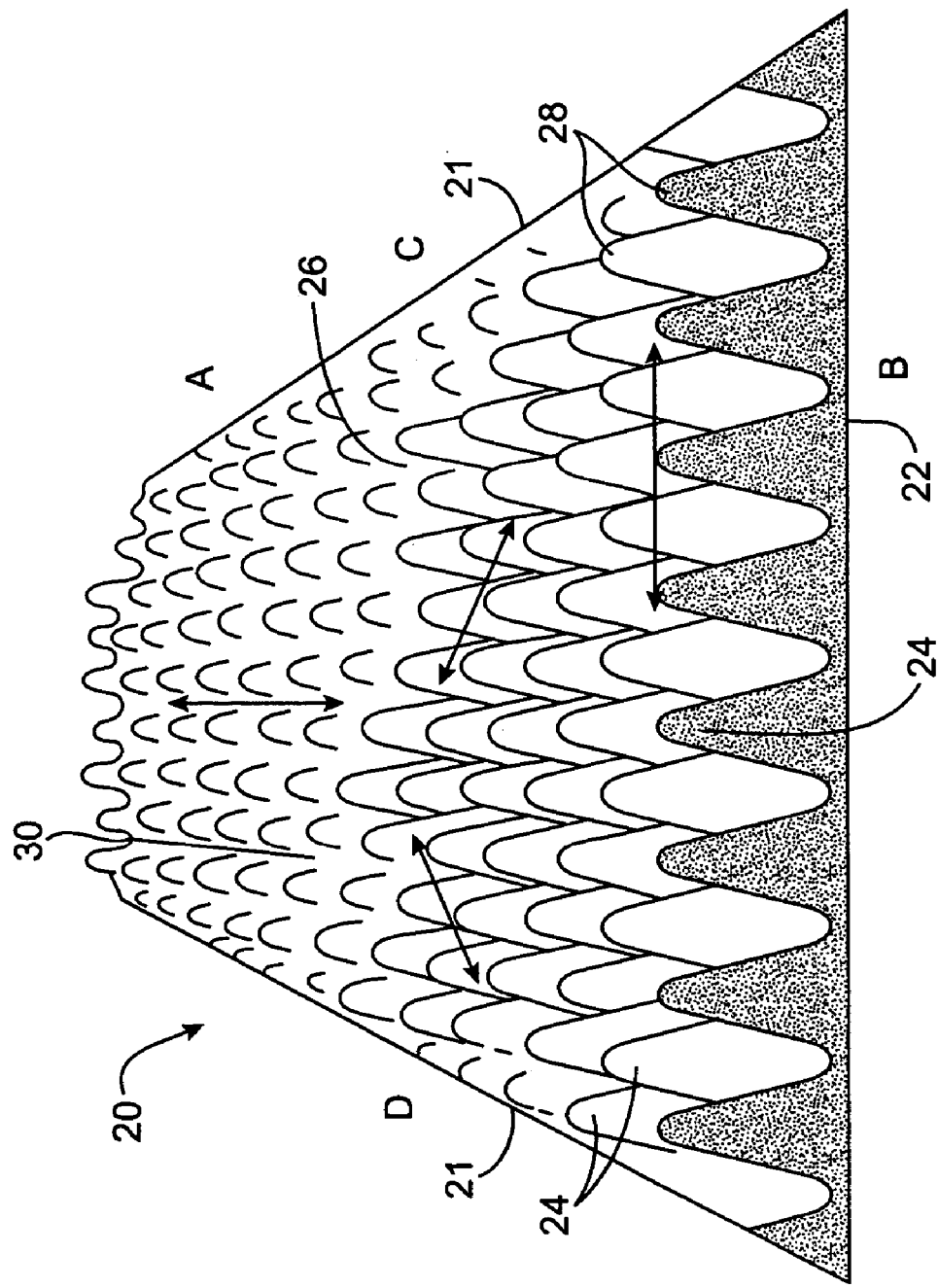
FIG. 3 is a detailed perspective view of a piece of convolute plastic foam material used in the construction of the therapeutic pressure sleeve.

As shown in FIG. 3, sleeve 18 is preferably made from a quadrangle of convoluted foam material 20 such as is widely used as an under-sheet lining on mattresses. Specifically, tapered quadrangle 20 of convoluted foam is cut as shown, with the sides 21 being angle-cut so that the edges meet flush when the foam is rolled to form a tapered sleeve. The foam comprises a base portion 22 having a multiplicity of convolutes or upward-standing fingers 24. Fingers 24 are arranged in a grid pattern formation as shown, having space 26 around each finger end 28. Since the fingers are arranged in rows, avenues or channels of space 30 exist in four different directions between and through these rows as indicated by arrows A, B, C, and D, which lie longitudinally, transversely, diagonally to the right and diagonally to the left.

Figure 4:
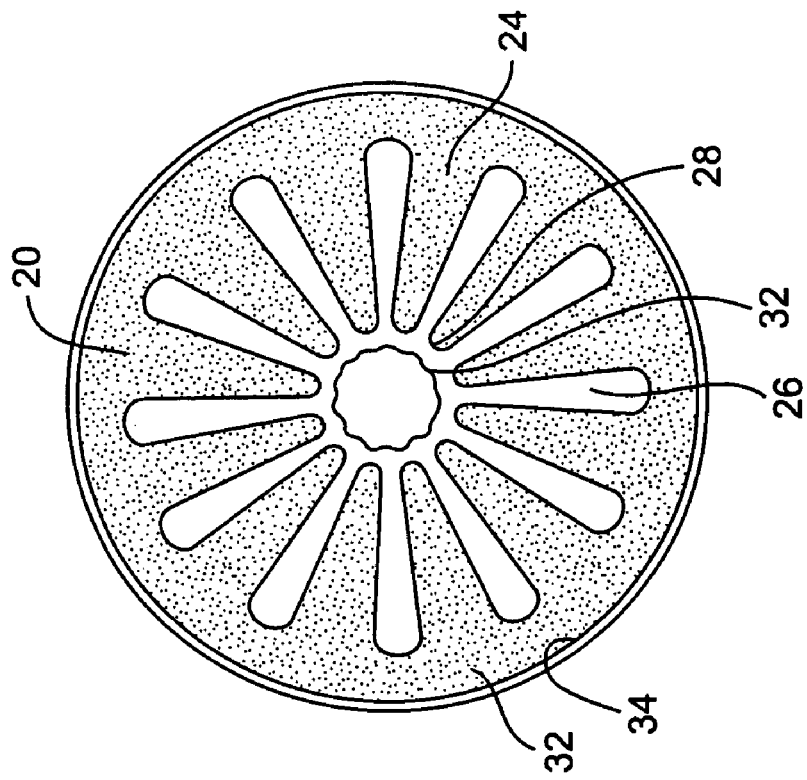
FIG. 4 is a sectional view of the therapeutic pressure sleeve similar to FIG. 1, but prior to its being received over the patient's arm.

As shown in cross section in FIG. 4, convoluted foam quadrangle 20 is rolled longitudinally, to form a slow-tapering funnel-shaped sleeve 18 with fingers 24 facing inwardly. As can also be seen, sleeve 18 is preferably encased in fabric comprising an inner lining 32 of SPANDEX material, and an outer lining 34 of NYLON. Any other suitable materials can also be used. Inner lining 32 and outer lining 34 are sewn together at each end, indicated by numeral 36 in FIG. 2A.

Foam quadrangle 20 of sleeve 18 is preferably dimensioned such that some stretching is required slip sleeve 18 over the patient's limb, yet still be easily slid on and off. Convoluted foam material can be made in a variety of material density, resulting in harder or softer pressure fingers. Soft fingers are used for patients requiring a lower level of applied pressure while more dense fingers are used for patients requiring high levels of applied pressure.

When the plane of convoluted foam material shown in FIG. 3, is rolled into a sleeve with the fingers facing inwardly, the fingers and the finger ends 28 are then located closer together as seen in FIG. 4. However, the fingers still maintain the original grid formation, and also a space between the fingers, and between the rows of fingers still exist in the four directions mentioned above.

A therapeutic pressure is applied by sleeve 18 as follows. When a limb, such as arm 25 (seen in FIGS. 5A, 5B and 5C) is placed inside sleeve 18, the elastomeric pressure fingers 24 press against skin 29 around and along the full length of the arm. Shaded areas 31 indicate the regions under direct pressure from fingers 24. Each pressure finger 24 is separated from the adjacent pressure finger by channel 30 against which no pressure is applied, and which therefore form the channels for conveying lymphedema fluids. It is believed that each small area under pressure changes the interstitial pressure in the tissues, moving lymphatic fluids into and along these channels to the lymphatic and venous drainage system.

Figure 5A:
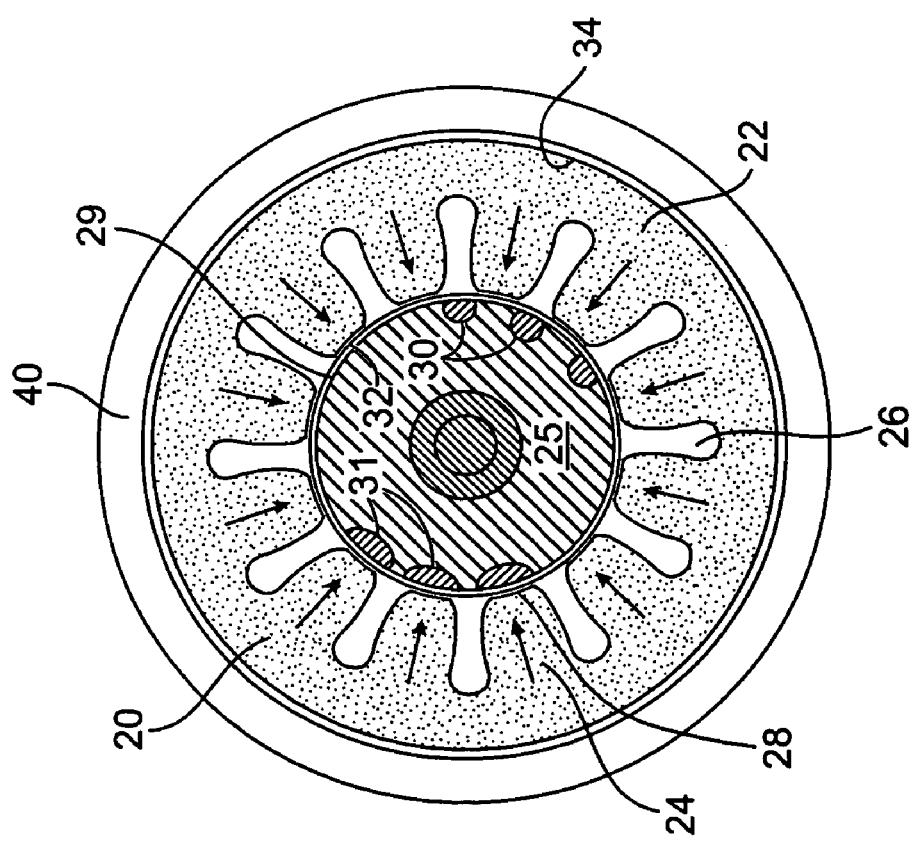
FIG. 5A is a sectional view taken along the line 5A-5A of FIG. 2A, showing the thin compression sleeve received over the therapeutic pressure sleeve, as together received over the patient's arm.

In a first embodiment of the secondary sleeve, as is shown in FIGS. 2A and 5A, a thin fabric compression sleeve 40 is pulled into position over sleeve 18 (after sleeve 18 has already been pulled into position over arm 25). Sleeve 18 will apply a therapeutic pressure to the patient's body surface (as has been described). Sleeve 40 is preferably formed from a thin sheet of LYCRA, or other elastically resilient, low friction material, cut and sewn together into a tapering, open-ended, generally cylindrically-shape. Sleeve 40 will preferably be dimensioned to have a diameter somewhat smaller than sleeve 18. Accordingly, sleeve 40, when stretched into position over sleeve 18, will tend to constrict, thereby applying a pressure to sleeve 18, thereby sleeve 18's therapeutic pressure delivered to the patient's limb. Receiving sleeve 18 into second sleeve 40, provides a combined pressure sufficient that the pressure applied by the fingers to the body surface is in the range from 5 mmHg to 60 mmHg, preferably from 10 mmHg to 45 mmHg. When using sleeves 18 and 40 in combination, it is preferable that sleeve 18 be constructed to apply a pressure in the range of 5 mmHg to 30 mmHg, with sleeve 40 applying an additional pressure in the range of 5 mmHg to 30 mmHg, thereby increasing the total therapeutic pressure on the limb to 10 mmHg to 60 mmHg. The pressure should be applied for a time sufficient to reduce swelling, typically being employed overnight. Often, initial treatment will involve daily (or nightly) treatments, with maintenance treatments occurring once or twice a week.

Sleeve 40, being fabricated from a low friction material such as LYCRA can easily be slipped on and off over the outer surface of sleeve 18. Accordingly, sleeves 18 and 40 together provide an effective system for applying a therapeutic pressure to a patient's limb, wherein the therapeutic pressure is higher than the pressure applied by sleeve 18 alone, thereby enabling sleeve 18 to be first easily slipped over the patient's limb and sleeve 40 to be subsequently easily slipped over sleeve 18.

Figure 5B:
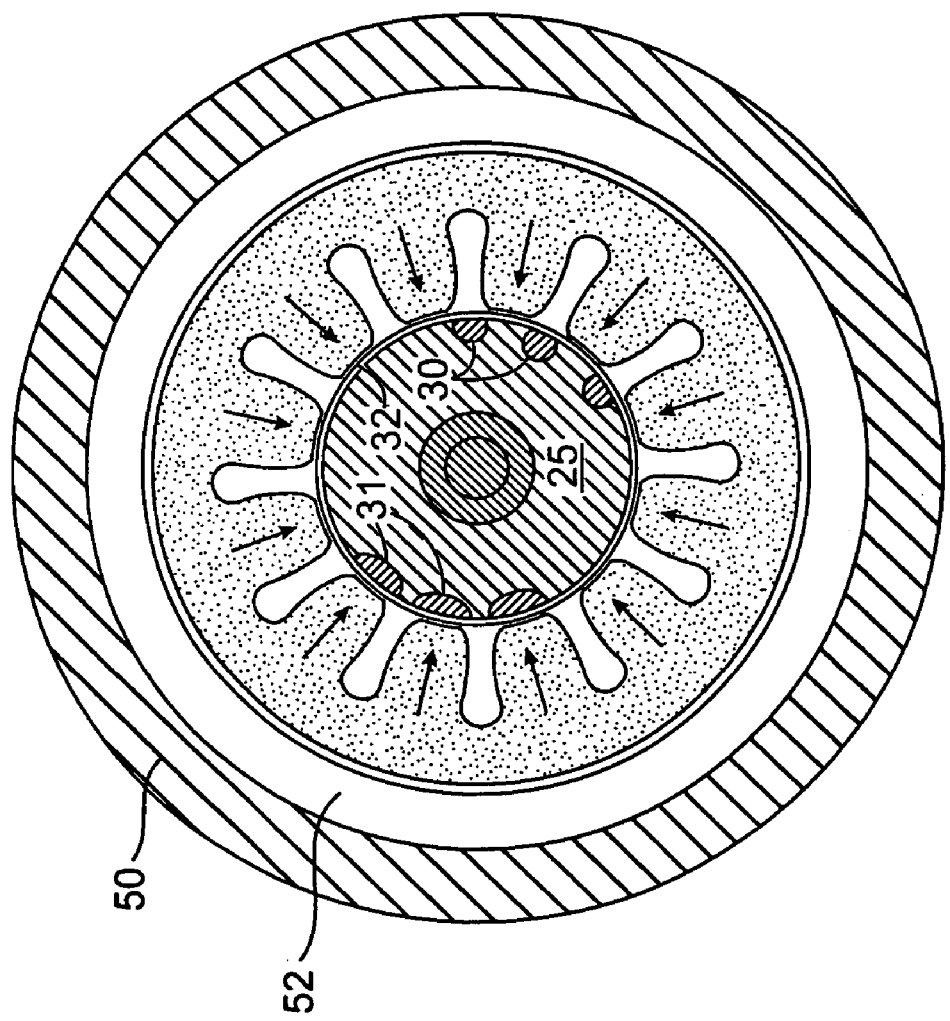
FIG. 5B is a sectional view taken along the line 5B-5B of FIG. 2B, showing the inflatable compression sleeve being in a substantially deflated condition.
Figure 5C:
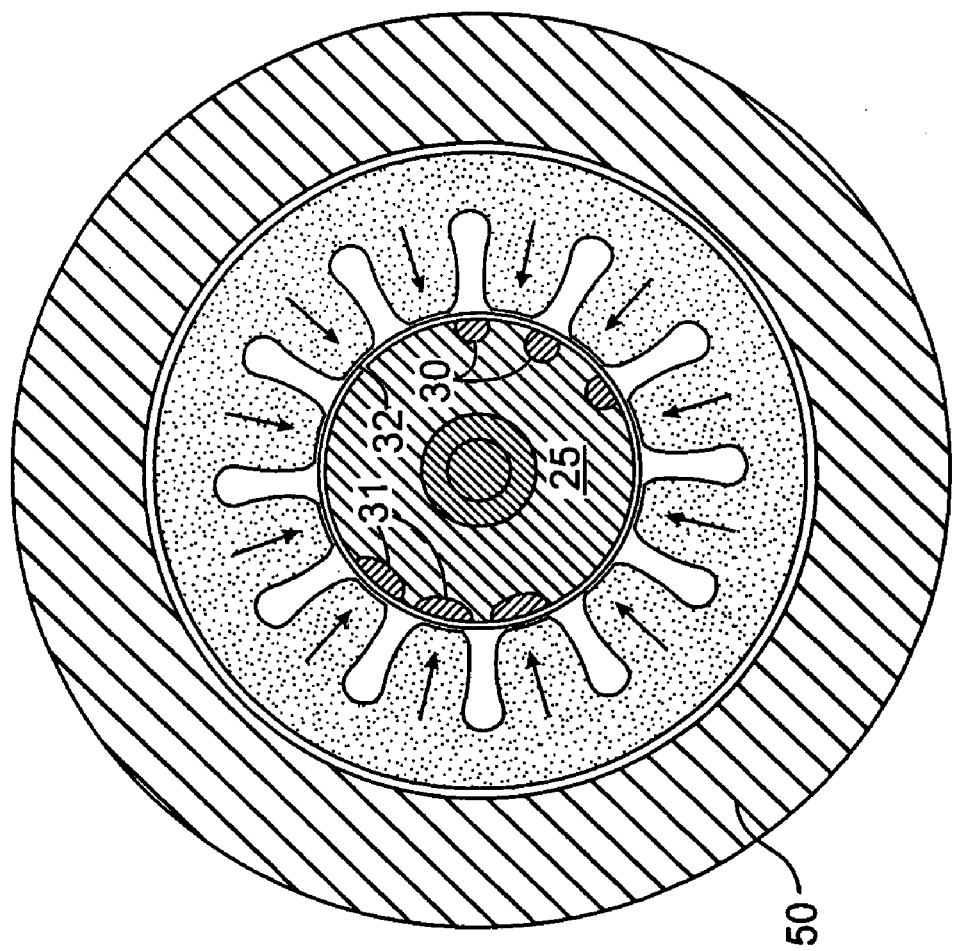
FIG. 5C is a sectional view taken along the line 5C-5C of FIG. 2B, showing the inflatable compression sleeve being in a substantially inflated condition.

In an alternate embodiment of the secondary sleeve, as shown in FIGS. 2B, 5B and 5C, a secondary sleeve 50 can be received over sleeve 18. Sleeve 50 is inflatable such that when deflated, as shown in FIG. 5B, it can loosely be received over sleeve 18, as illustrated by the presence of an air gap 52. When inflated, as shown in FIG. 5C, sleeve 50 will expand in volume such that any gaps between sleeve 50 and sleeve 18 will vanish, and sleeve 50 will exert an inward pressure on sleeve 18. By increasing the inflation pressure in sleeve 50, a greater amount of pressure can be applied to sleeve 18, thereby increasing the therapeutic pressure applied to the patient's body surface. As can be seen in FIG. 2B, sleeve 50 may optionally be divided into separate internal compartments 54, (shown for illustration as bands around the patient's limb), such that different inflation levels can be maintained in the separate compartments 54. Therefore, higher pressures can be applied at localized regions of the limb, as desired. Moreover, an external inflation system (not shown) can be used such that the inflation levels of each of the various compartments can be continuously varied over time so as to create a therapeutic massaging effect.

Figure 8:
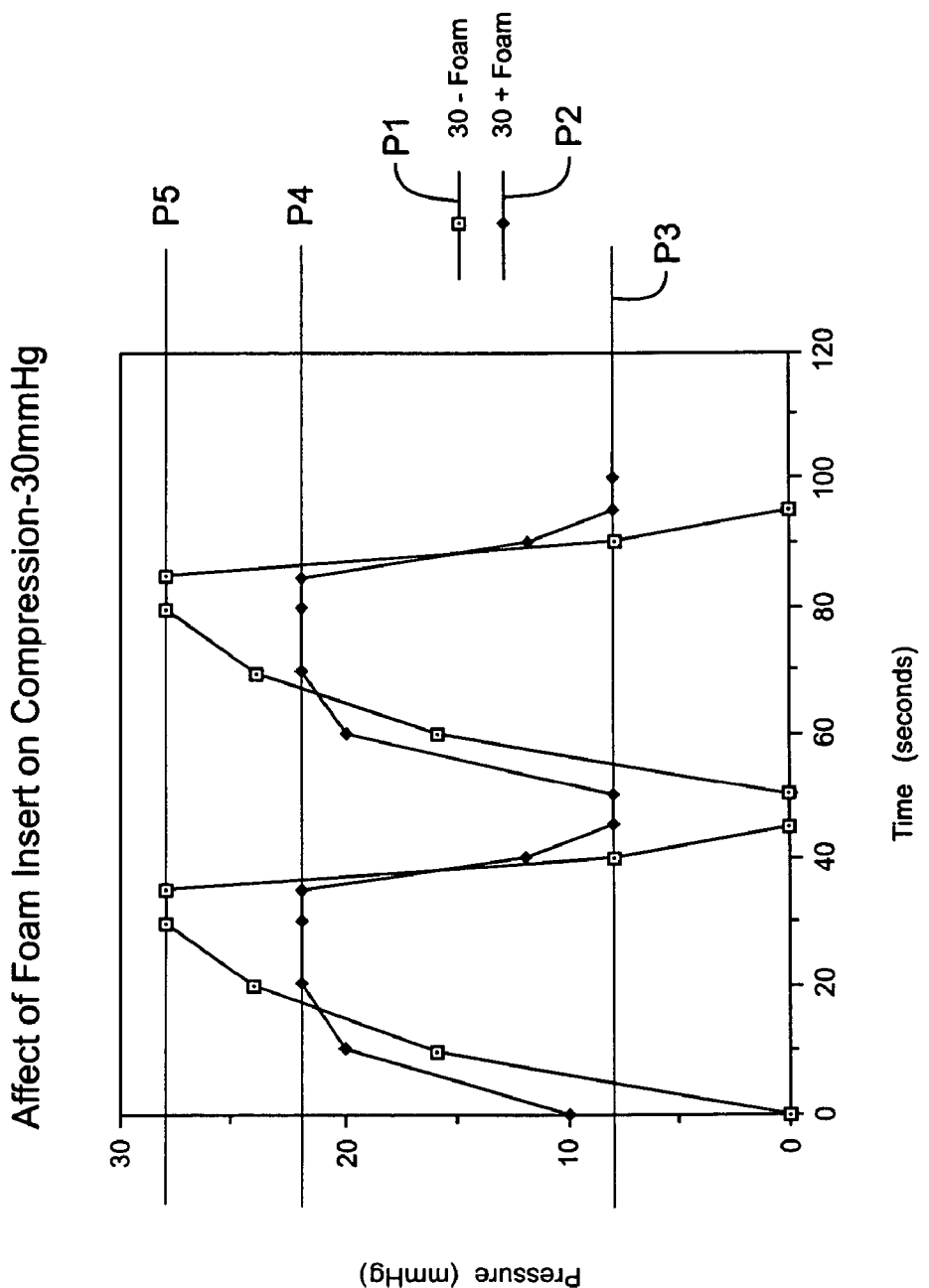
FIG. 8 is a graph of a periodic pressure applied to a patient's limb by an inflatable compression sleeve alone as compared to the periodic pressure applied to the patient's limb by an inner therapeutic pressure sleeve received within a inflatable outer compression sleeve.

When using sleeve 18 within sleeve 50, sleeve 50 can be intermittently inflated and deflated to generate a therapeutic massaging effect on the limb as illustrated in FIG. 8, as follows. Pressure P1 represents the pressure applied to a patient's limb when an inflatable compression sleeve (such as sleeve 50) is used alone on the patient's limb as the inflatable compression sleeve is repeatedly inflated and deflated. Pressure P2 represents the pressure applied to a patient's limb when the present inner therapeutic pressure sleeve 18 is received within inflatable outer compression sleeve 50.

As can be seen, pressure P1 will rise steeply to P5 as the inflatable outer compression sleeve is inflated from a pressure of 0 mmHg to pressure P5. As can also be seen, pressure P1 will also tend to fall off steeply as the inflatable outer compression sleeve pressure is reduced from P5 to 0 mmHg. In accordance with the present invention, when therapeutic compression sleeve 18 is received within an inflatable compression sleeve 50, pressure P2 will instead maintain a baseline therapeutic pressure P3 when inflatable compression sleeve 50 is deflated and will exert a maximum pressure of P4 when inflatable compression sleeve 50 is inflated. Accordingly, when using an intermittently inflating and delating compression sleeve to surround the limb, the use of the present inner therapeutic pressure sleeve 18 received therein will limit the maximum pressure applied to the limb, (from P5 to P4), and provide a baseline therapeutic pressure (P3). Furthermore, the maximum pressure change applied to the limb will be attenuated since in the absence of sleeve 18, the net pressure exerted by sleeve 50 on the limb will range from zero mmHg to P5, whereas, with sleeve 18 received within sleeve 50, the pressure will move in a much narrower range from P3 to P4. Accordingly, gentler and more gradual increases and decreases in the net pressure applied to the limb will be achieved than could be achieved by the use of an inflatable compression sleeve alone. Accordingly, a very beneficial therapeutic massaging effect can be generated.

Figure 6:
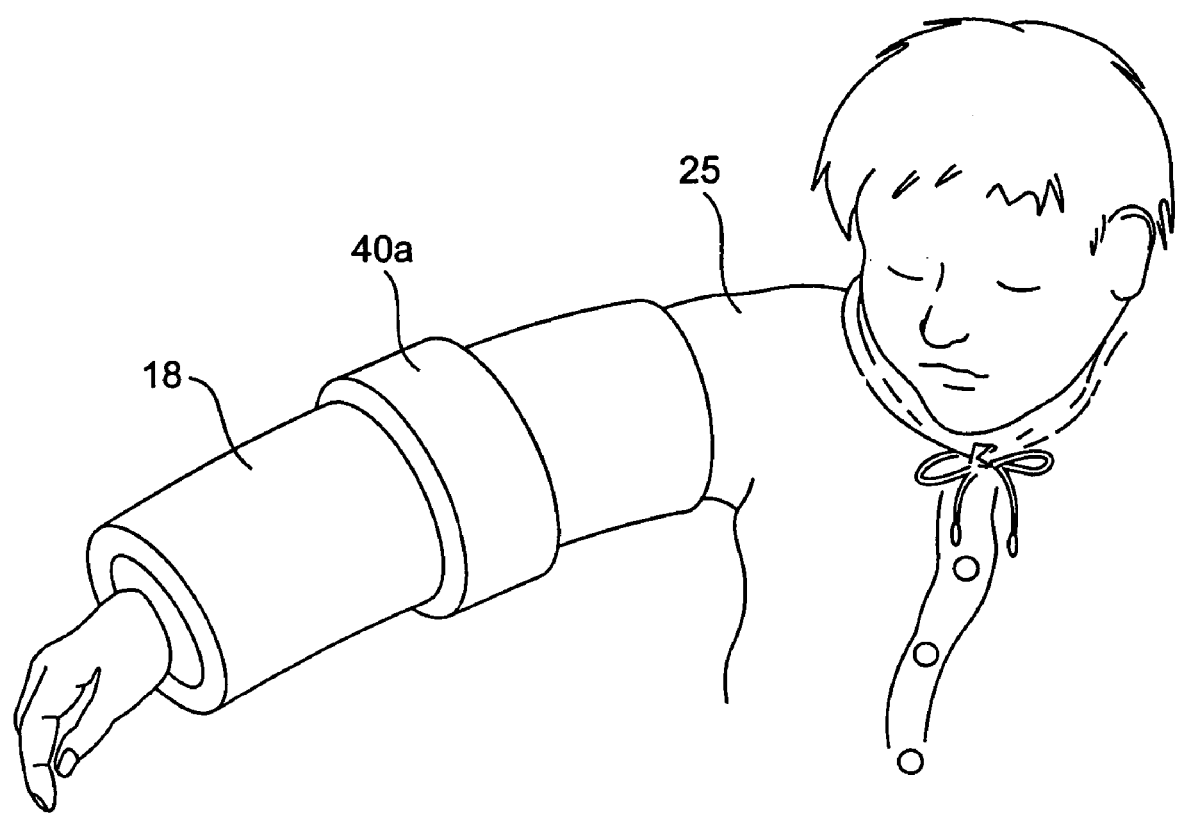
FIG. 6 is a perspective view of a shortened thin fabric compression sleeve received over the therapeutic pressure sleeve.

As is shown in FIG. 6, a shortened sleeve 40a, (identical in construction to sleeve 40, but of a shorter length than sleeve 18), can be used with sleeve 18 so as to produce a band of localized pressure at a particular region along arm 25. As can also be appreciated, a plurality of separate sleeves, each similar to sleeve 40a may be received over sleeve 18 at different locations, such that various therapeutic pressure bands are created along arm 25. As can also be appreciated, a plurality of sleeves 40a, (which can be of various lengths equal or shorter than sleeve 18), can be applied one over another at various locations on sleeve 18. Accordingly, the addition or removal of separate sleeves 40a can achieve increased pressures (when two or more sleeves 40a are received one over another). Moreover, finer pressure adjustment can be accomplished with the addition or removal of multiple sleeves since each of the plurality of sleeve can be designed to increase the pressure on the limb in small increments.

Figure 7:
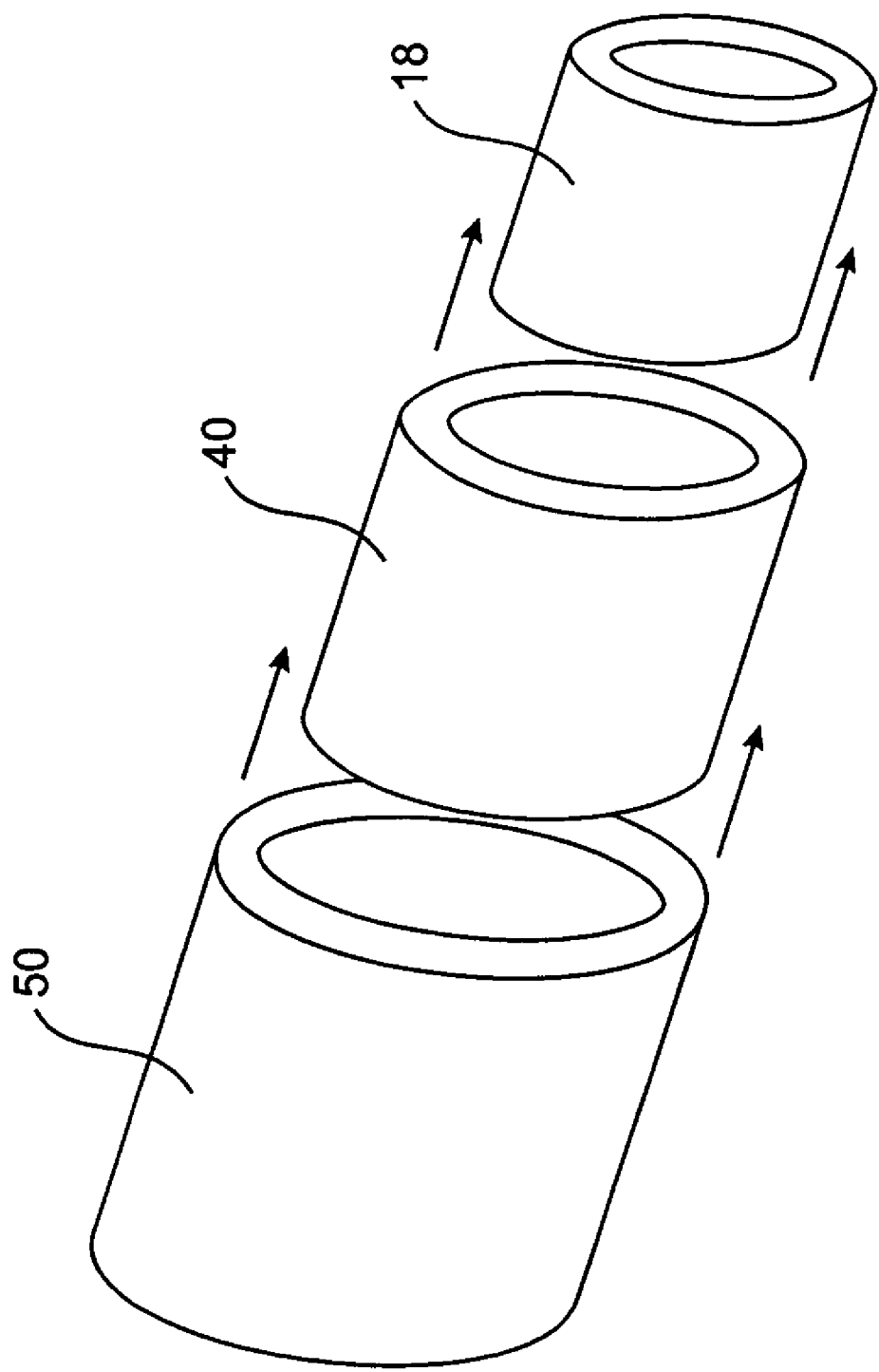
FIG. 7 is an exploded perspective side view of a therapeutic pressure sleeve received within a thin fabric compression sleeve which is in turn received within an inflatable compression sleeve.

In yet another embodiment of the present invention, as can be seen in the exploded view of FIG. 7, secondary sleeves 40 and 50 can be used together, with sleeve 40 preferably received within sleeve 50, as shown. Moreover, a plurality of shortened thin fabric compression sleeves 40a could also be used together with one inflatable compression sleeve 50. Such an arrangement would offer the benefits of various therapeutic pressure bands on the patient's limb (caused by sleeves 40a), coupled with a massaging effect (caused by sleeve 50).

The device illustrated in FIGS. 2A and 2B has been successfully employed in a number of test cases. Although the present invention is especially directed toward the treatment of lymphedema, it is envisioned as also being applicable for prevention and/or treatment of embolism or thrombosis, as well as for treatment of swollen limbs resulting from venous insufficiency.

Those skilled in the art will envision that many other possible variations are within its scope. For example skilled artisans will readily be able to change the thickness or density of the foam, or length of convolutes, or assembly different combinations of foam, or design a different configuration of pressure points and channels. Moreover, any suitable material can be used to cover the elastomeric pressure material, including fabric printed with patterns. Other types of foam material such as rubber, plastic air bubbles, foam air bubbles or non-convolute foam and the like can be used. Different means of installation can be used. Various heights of convolutes can be used to conform to limb shape, and various number of convolutes per square foot can be used. Although not necessary for the present invention, it is also possible to use VELCRO bands, other tightening bands, and zippers around or along the outermost sleeve, as a system for further increasing pressure on the limb.

Accordingly, the reader is requested to determine the scope of the invention by the appended claims and their legal equivalents, and not by the examples which have been given.

What is claimed is:

1. A system for applying pressure to a body limb, said system comprising:
   a first sleeve comprising a cylindrical body open at both ends, having a foam lining, and being configured to be slid over the full length of the limb and to apply an inward pressure onto the limb; and
   a second sleeve comprising a cylindrical body open at both ends and being configured to be slid wholly over the entire length of the first sleeve such that the second sleeve will have the same length as the first sleeve and will apply additional inward pressure along the full length of the limb when the second sleeve is in place over the first sleeve.

2. A system as in claim 1, wherein the first sleeve is configured to cover an arm from the wrist to near the shoulder.

3. A system as in claim 1, wherein at least the first sleeve has an outer surface with a low coefficient of friction.

4. A system as in claim 3, wherein at least the second sleeve consists essentially of thin fabric sleeves.

5. A system as in claim 4, wherein each of the sleeves independently provides an inward pressure in the range from 5 mmHg to 30 mmHg.

6. A system for applying pressure to an arm, said system comprising: an innermost therapeutic pressure sleeve (TPS) comprising a cylindrical body open at both ends having ridges formed over an inner surface and configured to be slid over the entire length of the arm from the shoulder to the wrist and to apply an inward pressure thereon; and at least a second sleeve comprising a cylindrical body open at both ends being configured to be slid wholly over the entire length of the TPS such that the second sleeve will have the same length as the therapeutic pressure sleeve and will apply additional inward pressure onto the limb when the second sleeve is in place over the therapeutic pressure sleeve.

7. A system as in claim 6, wherein the TPS has an outer surface with a low coefficient of friction.

8. A system as in claim 7, further comprising at least a third sleeve configured to be slid over the second sleeve to apply additional inward pressure onto the limb.

9. A system as in claim 8, wherein the second and third sleeves consist essentially of thin fabric sleeves.

10. A system as in claim 9, wherein each of the TPS and sleeves independently provide an inward pressure in the range from 5 mmHg to 30 mmHg when placed over the arm.

* * * * *